(12) United States Patent
Sorensen et al.

(10) Patent No.: US 6,858,587 B2
(45) Date of Patent: Feb. 22, 2005

(54) USE OF TISSUE FACTOR AGONIST OR TISSUE FACTOR ANTAGONIST FOR TREATMENT OF CONDITIONS RELATED TO APOPTOSIS

(75) Inventors: Brit Binow Sorensen, Birkerod (DK); Lars Christian Petersen, Horsholm (DK)

(73) Assignee: Novo Nordisk Pharmaceuticals, Inc., Princeton, NJ (US)

( * ) Notice: Subject to any disclaimer, the term of this patent is extended or adjusted under 35 U.S.C. 154(b) by 0 days.

(21) Appl. No.: 10/285,970

(22) Filed: Nov. 1, 2002

(65) Prior Publication Data

US 2003/0125255 A1 Jul. 3, 2003

Related U.S. Application Data

(60) Provisional application No. 60/335,385, filed on Nov. 15, 2001.

(30) Foreign Application Priority Data

Nov. 2, 2001 (DK) .......................... 2001 01628

(51) Int. Cl.$^7$ ............................................. A61K 38/00
(52) U.S. Cl. ........................... 514/12; 514/18; 530/331; 530/384; 424/94.64
(58) Field of Search ..................... 514/12, 18; 530/331, 530/384; 424/94.64

(56) References Cited

U.S. PATENT DOCUMENTS 6,106,830 A * 8/2000 Li ............................. 424/94.64
6,268,163 B1 * 7/2001 Kongsbak et al. ............. 435/15

FOREIGN PATENT DOCUMENTS

| WO | WO 94/05328 A1 | 3/1994 |
| WO | WO 94/27631 A1 | 12/1994 |
| WO | WO 99/03498 A1 | 1/1999 |
| WO | WO 99/16789 A1 | 4/1999 |
| WO | WO 01/05353 A2 | 1/2001 |
| WO | WO 01/30333 A2 | 5/2001 |

OTHER PUBLICATIONS

Mueller et al. J. Clin. Invest. 101(7):1372–1378 1998.*
Kulik et al. Molecular and Cellular Biology 17:1595–1606 1997.*
Versteeg et al. J. Biol. Chem. 275:28750–28756 2000.*
Bromberg, M. et al. PNAS 92(18): 8205–8209 1995.*
Siegbahn, A. Haemostasis 30(suppl 2):41–47 2000.*
Cooper, Geoffrey M., The Cell, Part IV, Chapter 13, 2$^{nd}$ Edition, BU 2000.
Eastman, Alan & Rigas, James R., Semin Oncol, vol. 26 (5 suppl. 16), pp. 7–16, dis. 41 & 42 (Oct. 1999).
Héron–Milhavet et al., J. Biol Chem, vol. 276 (19), pp. 18185–18192 (May 25, 2001).
Korsmeyer, Stanley J., Cancer Res., vol. 59 (7 suppl.), pp. 1693s–1700s (Apr. 1, 1999).
Li et al., Arterioscler Throm Vasc Biol., vol. 23 (12), pp. 2178–2184 (Dec. 2003).
Lopaczynski, Wlodzimierz, Acta Biochim Pol, vol. 46 (1), pp. 51–60 (1999).
O'Connor et al. Biochem Soc Trans, vol. 28 (2), pp. 47–51 (Feb. 2000).
Platanias, Leonidas C., Blood, vol. 101 (12), pp. 4667–4679 (Jun. 15, 2003).
Satymoorthy et al., Cancer Res., vol. 61 (19), pp. 7318–7324 (Oct. 1, 2001).
Shack et al., Mol Cell Biol., vol. 23 (7), pp. 2407–2414 (Apr. 2003).
Versteeg et al., Carcinogenesis, vol. 24 (6), pp. 1009–1013 (2003).
Versteeg et al., J. Biol. Chem., vol. 277 (30), pp. 27065–27072 (2002).
Versteeg et al., Oncogene, vol. 23 (2), pp. 410–417 (2004).
Versteeg et al., Thromb Haemost, vol. 86 (6), pp. 1353–1359 (Dec. 2001).
Kawada et al., Japanese Journal of Clinical Hematology, vol. 30, No. 11, pp. 1982–1986 (1989) (translation).
Takeya et al., Thrombosis and Apoptosis, vol. 45, No. 7, (1997) Retrieved from the Internet (translation).
Walther et al., Archiv Fur Klinische Medizin, vol. 215, pp. 161–173 (1968) (translation).
Libby et al., Current Opinion in Lipidology, vol. 7, No. 5, pp. 330–335 (1996).
Bromberg et al., Proc. Natl. Acad. Sci. USA, vol. 92, pp. 8205–8209 (1995).
Greeno et al., Laboratory Investigation, vol. 75, No. 2, pp. 281–289 (1996).
Kockx et al., Circulation, vol. 102, No. 13, p. e99 (2000).

* cited by examiner

Primary Examiner—Karen Cochrane Carlson
Assistant Examiner—Anand Desai
(74) Attorney, Agent, or Firm—Len Smith; Reza Green; Richard Bork

(57) ABSTRACT

The present invention relates to use of FVII and/or FVIIa and/or another TF agonist and/or FVIIai and/or another TF antagonist in therapeutic treatment of pathological conditions increased or decreased cell apoptosis is required.

10 Claims, 14 Drawing Sheets

Apoptosis illustrated by FITC-dUTP staining of BHK(+TF)
Dose-response of FVIIa
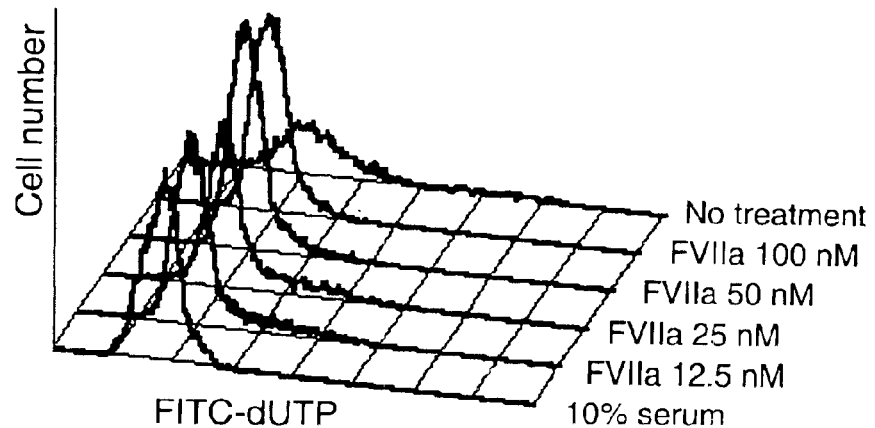
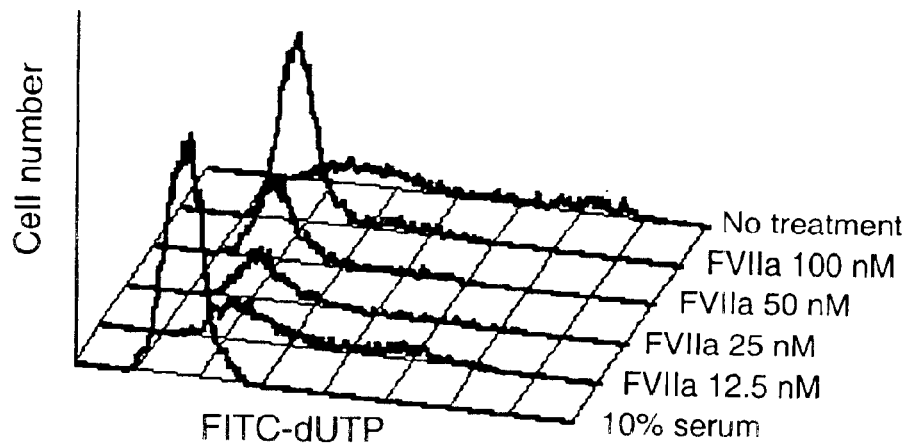
Fig. 1

Apoptosis illustrated by FITC-dUTP staining of BHK wt
Dose-response of FVIIa
Serum-starved for 24 hr with the indicated compounds
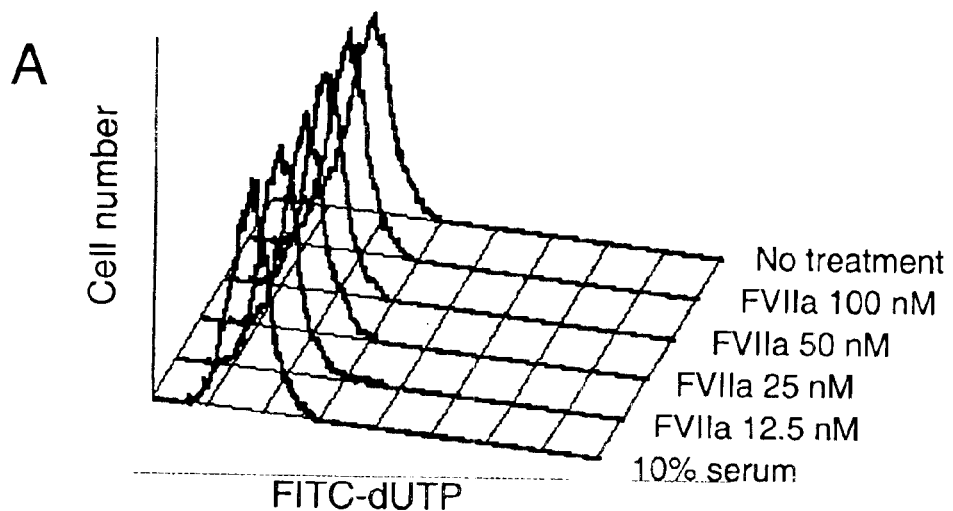
Serum-starved for 48 hr with the indicated compounds
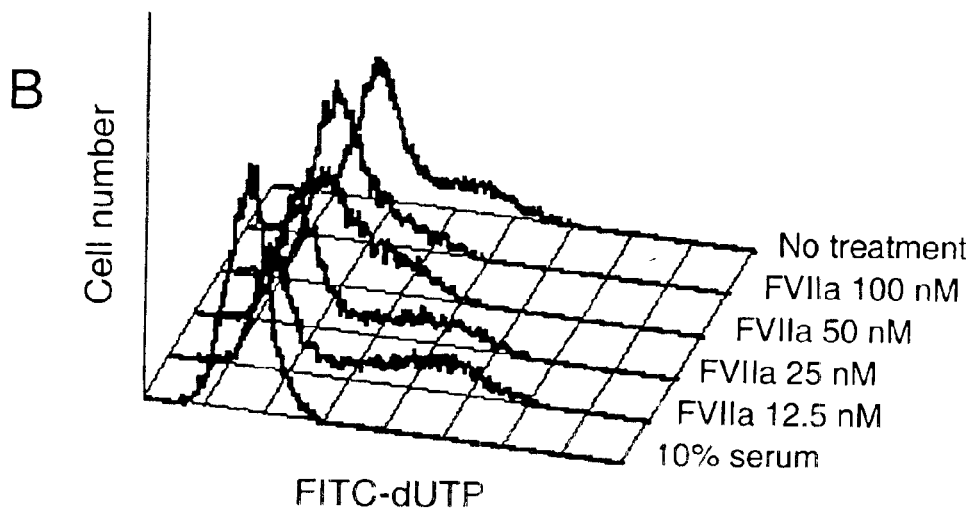
Fig. 2

Apoptosis illustrated by FITC-dUTP staining of BHK(+TF)
Involvement of FXa and thrombin inhibitors
Serum-starved for 24 hr with the indicated compounds
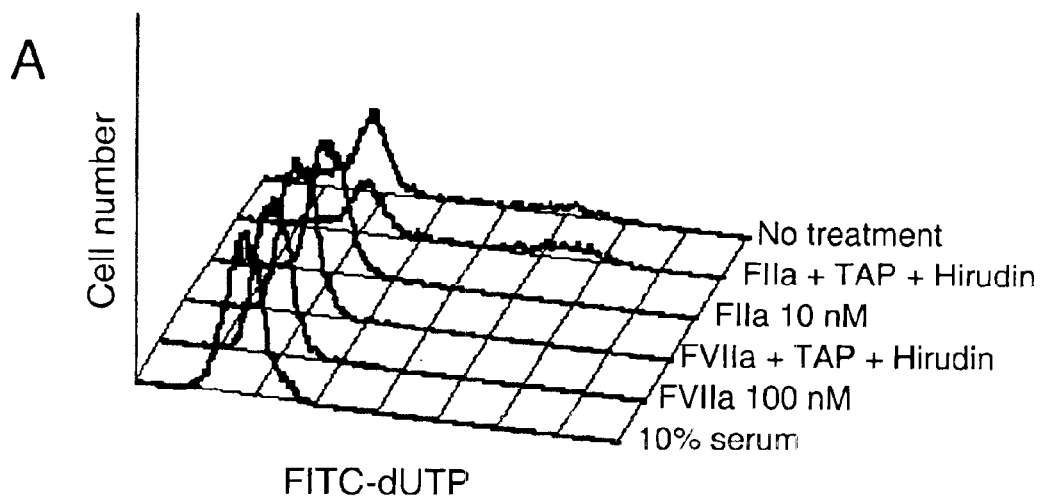
Serum-starved for 48 hr with the indicated compounds
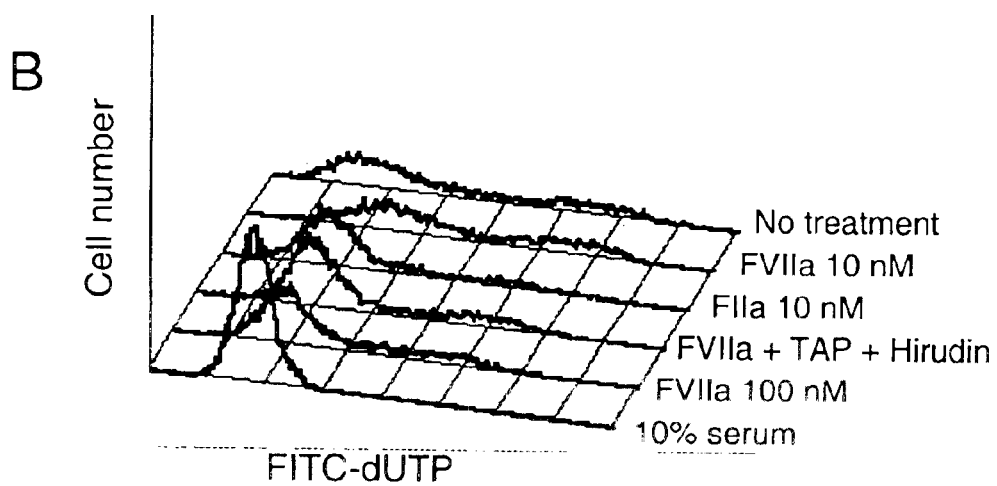
Fig. 3

Apoptosis illustrated by FITC-dUTP staining of BHK wt
Involvement of FXa and thrombin inhibitors
Serum-starved for 24 hr with the indicated compounds
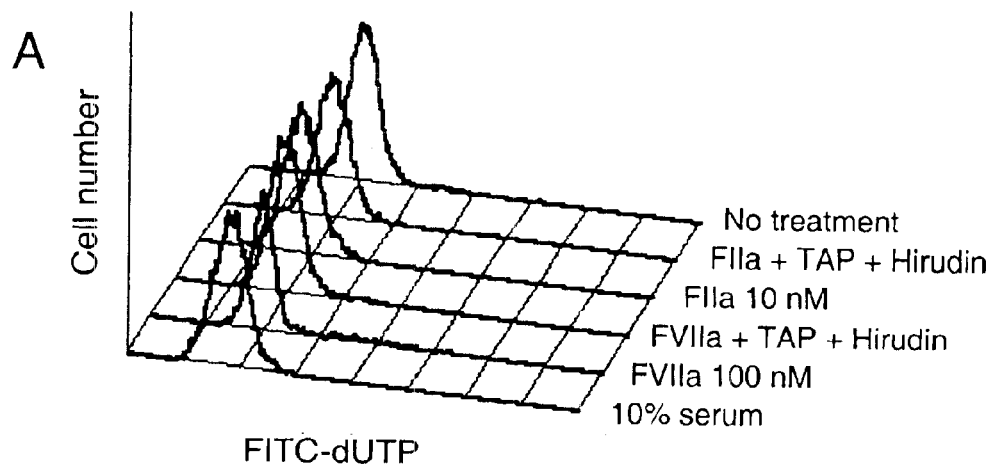
Serum-starved for 48 hr with the indicated compounds
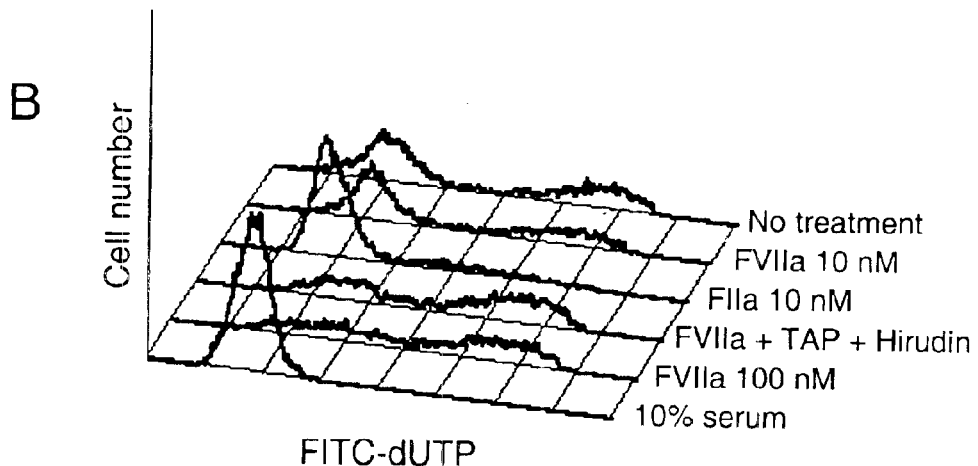
Fig. 4

Apoptosis illustrated by FITC-dUTP staining of BHK(+TF)
Effect of FVIIa and FFR-FVIIa on serum-starvation
induced apoptosis
Serum-starved for 24 hr with the indicated compounds
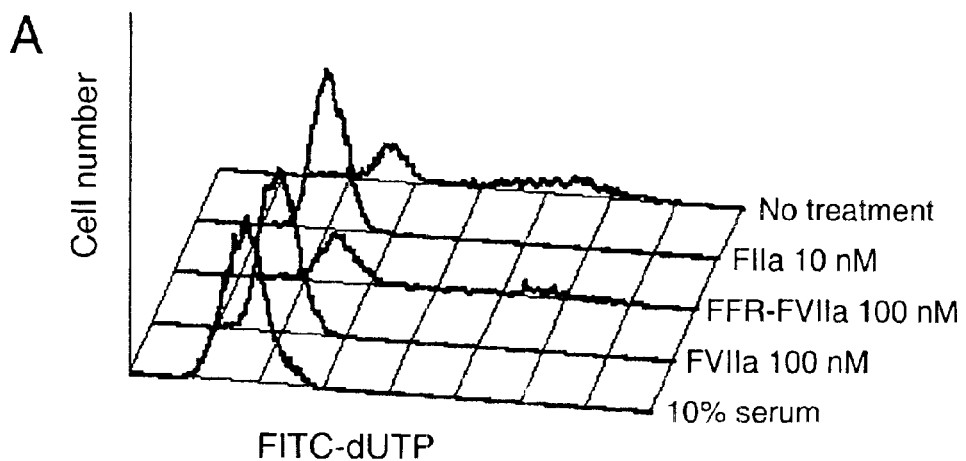
Serum-starved for 48 hr with the indicated compounds
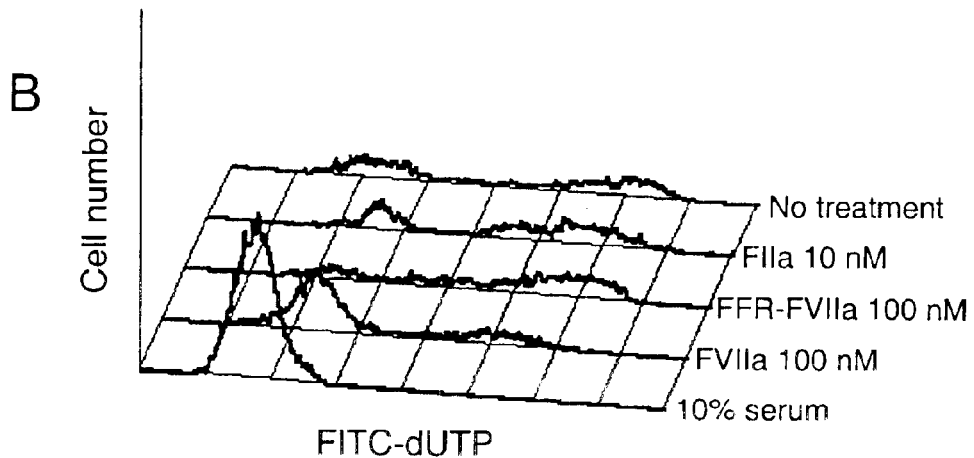
Fig. 5

Fig. 7   Apoptosis illustrated by Hoechst staining of condensed nuclei (marked with an arrow) in BHK(+TF) cells.

Fig. 8
Apoptosis illustrated by FITC-dUTP staining. Dose-dependent anti-apoptotic effect of FVIIa in cells expressing TF. TUNEL analysis by flow cytometry.
A: BHK(+TF), 24 hr
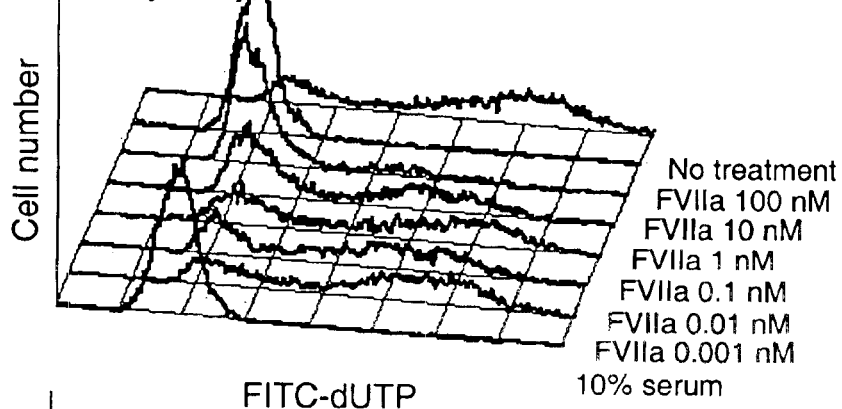
B: BHK(+TF), 48 hr
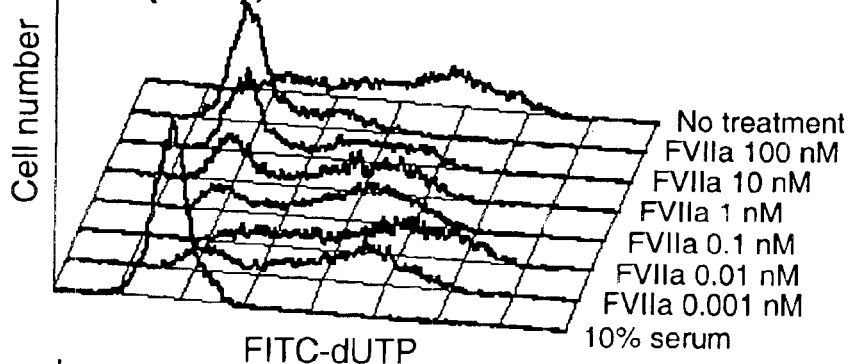
C: BHK wt, 48 hr
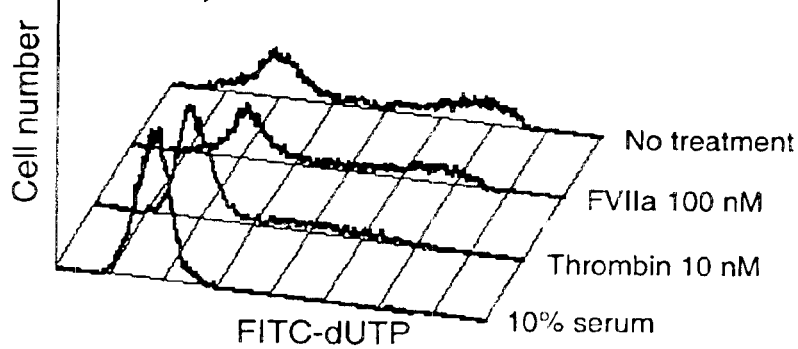

Apoptosis illustrated by FITC-dUTP staining of
BHK(+TF) analyzed by TUNEL and flow cytometry.
Involvement of FFR-FVIIa
Involvement of FXa and thrombin inhibitors
A: BHK(+TF), 24 hr
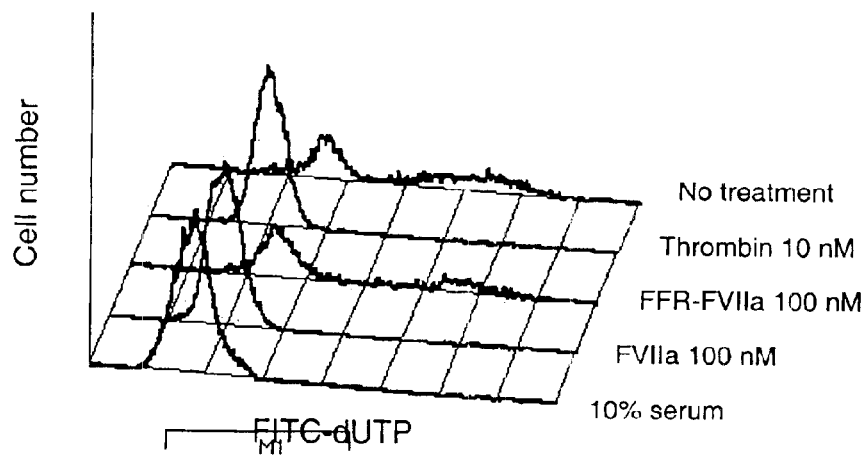
No treatment
Thrombin 10 nM
FFR-FVIIa 100 nM
FVIIa 100 nM
10% serum
B: BHK(+TF), 24 hr
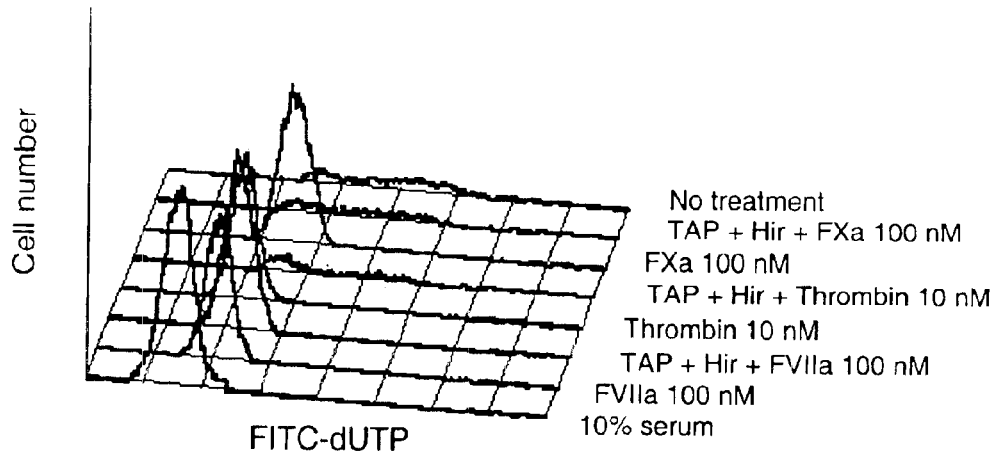
No treatment
TAP + Hir + FXa 100 nM
FXa 100 nM
TAP + Hir + Thrombin 10 nM
Thrombin 10 nM
TAP + Hir + FVIIa 100 nM
FVIIa 100 nM
10% serum
Fig. 9

Apoptosis illustrated by activation of caspase 3.
Western blot anlysis using anti-caspase 3 ab's.
Anti-apoptotic effect of FVIIa only in cells
expressing TF.
BHK(+TF)
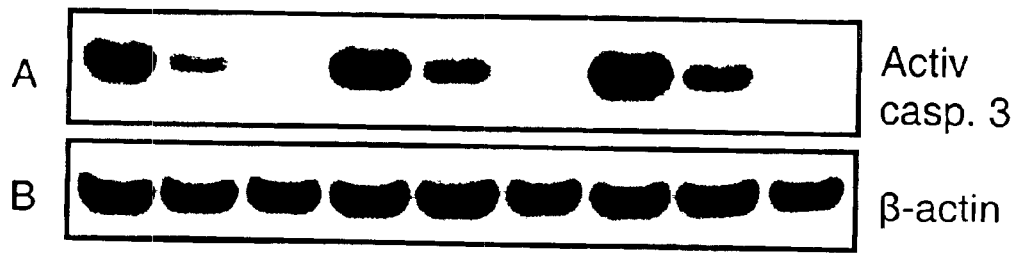
wt BHK
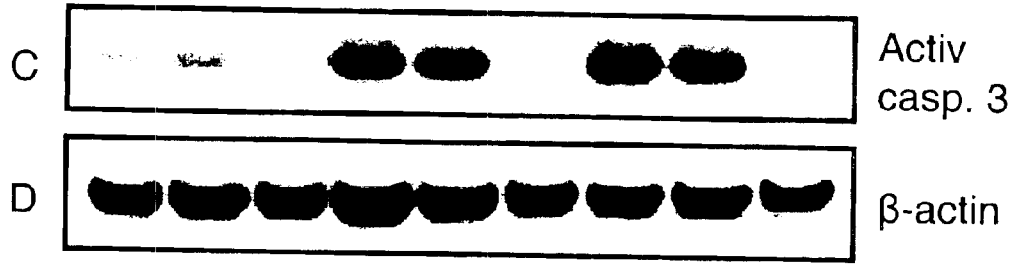
Fig. 11

The anti-apoptotic effect of FVIIa is dose-dependent and correlates with the ability of FVIIa to activate p44/42 MAPK and Akt in BHK(+TF) cells. Western blot analysis.
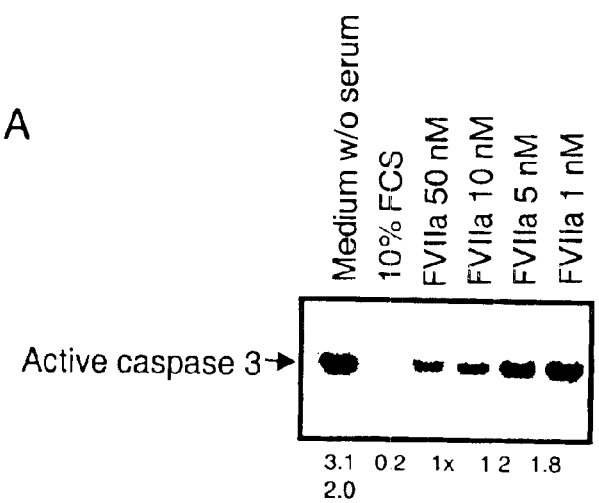
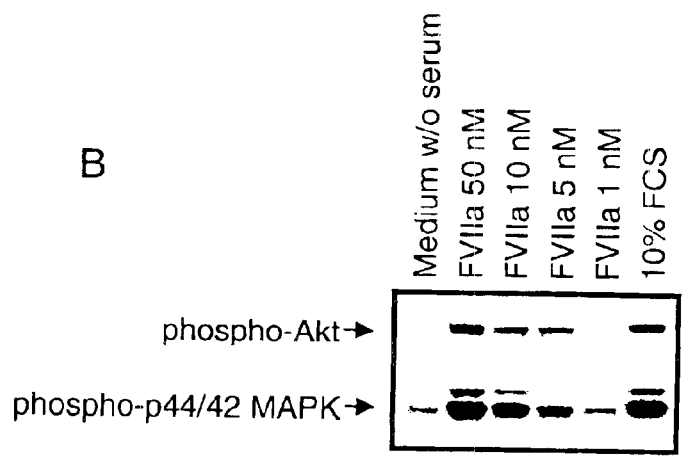
Fig. 13

USE OF TISSUE FACTOR AGONIST OR TISSUE FACTOR ANTAGONIST FOR TREATMENT OF CONDITIONS RELATED TO APOPTOSIS

CROSS-REFERENCE TO RELATED APPLICATION

This application claims priority under 35 U.S.C. 119 of Danish application no. PA 2001 01628 filed Nov. 2, 2001 and U.S. application No. 60/335,385 filed Nov. 15, 2001, the contents of which are fully incorporated herein by reference.

FIELD OF THE INVENTION

A novel cell regulating activity of a tissue factor (TF) agonist such as, for example, coagulation factor VII (FVII) or a tissue factor antagonist such as, for example, inactivated coagulation factor VIIa (FVIIai) on cells expressing tissue factor (TF) has been described. The present invention relates to a method for regulating cell apoptosis by contacting the cell with a TF agonist, e.g. FVIIa, or a TF antagonist, e.g. FVIIai. The invention also relates to the use of FVIIa or another TF agonist, or FVIIai or another TF antagonist for the preparation of a medicament for regulation of conditions related to apoptosis in a patient. Moreover the present invention relates to a method of treating conditions in a patient, where a decrease or an increase of apoptosis is required.

BACKGROUND OF THE INVENTION

The extrinsic pathway of blood coagulation is initiated when FVIIa circulating in plasma binds to the integral-membrane protein, tissue factor (TF). The involvement of FVIIa as a proteolytic enzyme in the blood coagulation cascade is believed to be confined to the extracellular leaflet of TF expressing cells. Studies of a putative intracellular signaling capacity of FVIIa have shown that it induce mobilization of intracellular free calcium ($Ca^{2+}$) in a human bladder carcinoma cell line, which constitutively express TF and in umbilical vein endothelial cells which were pretreated with interleukin-1 to express TF, but have failed to show any cytokine-like activation of intracellular tyrosine kinases. Recent reports indicate that TF may influence important biological functions other than coagulation, such as angiogenesis, embryo vascularization and tumor metastasis. At present, however, it is unclear how TF contributes to these biological processes.

A potential role for the TF cytoplasmic domain in signal transduction is indicated in studies that showed prometastatic function of TF is critically dependent on the TF cytoplasmic domain. Further, TF cytoplasmic domain is shown to interact with actin-binding protein 280 (ABP-280) and supports cell adhesion and migration through recruitment of ABP-280 to TF-mediated adhesion contacts.

However, TF has also been shown to participate certain types of cell signaling by serving as a cofactor for its physiological ligand FVIIa in an extracellular signaling by a putative proteolytic mechanism. For example, binding of FVIIa to cell surface TF is shown to induce intracellular $Ca^{2+}$ oscillations in a number of TF expressing cells, transient phosphorylation of tyrosine in monocytes, activation of MAP kinase, alteration in gene expression in fibroblasts and enhanced expression of urokinase receptor in tumor cells. Catalytically inactive FVIIa (FVIIai) fails to induce many of the above signaling responses, from $Ca^{2+}$ oscillations to MAP kinase activation and gene reduction, and it appears that the catalytic activity of FVIIa may be required for at least some TF-FVIIa-mediated signal transduction. At present, not much is known about signaling pathway(s) that are induced by proteolytically active FVIIa.

Normal tissues in the body are formed either by cells that have reached a terminally differentiated state and no longer divide or by cells that die after a period of time and are replaced from a pool of dividing cells. For example, nervous tissue is formed early in development and the cells of the nervous system reach a terminally differentiated state soon after birth. In general, when nervous tissue is damaged, the nerve cells are incapable of dividing and, therefore, the loss of function due to the damaged nerve cells is not repaired.

In comparison to the nervous system, the skin is composed of stratified layers of epithelial cells, in which the upper (outer) layer of cells constantly is sloughed off and the lower layer of cells divides so as to replace the lost cells. Thus, the skin is an example of a tissue that is maintained in a steady-state, where the number of cells that are lost is equivalent to the number of new cells produced.

In some tissues such as skin, the steady-state is maintained, in part, due to a process of programmed cell death, in which the cells are genetically "programmed" to die after a certain period of time. A cell experiencing programmed cell death undergoes morphologic changes characteristic of apoptosis, including, for example, fragmentation of its DNA and collapse of its nucleus.

Apoptosis is particularly prominent during the development of an organism, where cells that perform transitory functions are programmed to die after their function no longer is required. In addition, apoptosis can occur in cells that have undergone major genetic alterations, thus providing the organism with a means to rid itself of defective and potentially cancer forming cells. Apoptosis also can be induced due to exposure of an organism to various external stimuli, including, for example, bacterial toxins, ethanol and ultraviolet radiation. Chemotherapeutic agents for treating cancer also are potent inducers of apoptosis.

DESCRIPTION OF THE INVENTION

The present invention relates to usage of FVII and/or FVIIa and/or another TF agonist and/or FVIIai and/or another TF antagonist in therapeutic treatment of pathological conditions that can be related to apoptosis.

Generally, the blood components, which participate in what has been referred to as the coagulation "cascade" are proenzymes or zymogens, enzymatically inactive proteins, which are converted to proteolytic enzymes by the action of an activator, itself an activated clotting factor. Coagulation factors that have undergone such a conversion and generally referred to as "active factors", and are designated by the addition of the letter "a" to the name of the coagulation factor (e.g. factor VIIa).

The term "FVII" or "factor VII" means "single chain" (zymogenic) coagulation factor VII. The term "Factor VIIa", or "FVIIa" means "two chain" activated coagulation factor VII cleaved by specific cleavage at the Arg152-Ile153 peptide bond. FVII and FVIIa may be purified from blood or produced by recombinant means. It is evident that the practice of the methods described herein is independent of how the purified factor VIIa is derived and, therefore, the present invention is contemplated to cover use of any factor FVII or FVIIa preparations suitable for use herein. Preferred are human FVIIa.

The term "modified factor VII", "inactivated FVII", or "F VIIai" is intended to mean FVIIa having at least one modification, which modification substantially inhibits the ability of modified FVIIa to activate FX and/or FIX. This modification may be in the catalytic centre of FVIIa. The terms may be used interchangeably. Such modification includes amino acid substitution (or replacement) of one or more of the catalytic triad residues Ser344, Asp142 and His193, and also includes modification of catalytic triad residues with wine protease inhibitors such as organophosphor compounds, sulfanylfluoride, peptide halomethyl ketone or azapeptide. Modifications also includes amino acid deletions and insertions. FFR-FVIIa is one example of a FVIIai derivative obtained by blocking of the active centre of FVIIa with the irreversible inhibitor, D-phenylalanine-L-phenylalanine-L-arginine chloromethyl ketone (FFR cmk). Other suitable FVIIai derivates are inactivated FVIIa obtained or obtainable by blocking the active centre with L-phenylalanine-L-phenylalanine-L-arginine chloromethyl ketone, dansyl-L-phenylalanine-L-phenylalanine-L-arginine chloromethyl ketone, or dansyl-D-phenylalanine-L-phenylalanine-L-arginine chloromethyl ketone. Preferred is FFR-FVIIa (FVIIa inactivated by FFR cmk).

The term "TF agonist", as used herein is intended to mean any compound reducing or inhibiting apoptosis of a cell population as determined in the apoptosis assay described in example 3 by direct binding to TF (e.g. FVIIa) or other TF dependent mechanism.

In one embodiment of the invention, the TF agonist is recombinant factor VIIa. In a further embodiment the TF agonist is a factor VIIa equivalents. In one embodiment, the factor VII equivalents are amino acid sequence variants having no more than 20 amino acids replaced, deleted or inserted compared to wild-type factor VII (i.e., a polypeptide having the amino acid sequence disclosed in U.S. Pat. No. 4,784,950). In another embodiment, the factor VIIa variants have no more than 15 amino acids replaced, deleted or inserted; in another embodiment, the factor VII variants have no more than 10 amino acids replaced, deleted or inserted; in another embodiment, the factor VII variants have no more than 8 amino acids replaced, deleted or inserted; in another embodiment, the factor VII variants have no more than 6 amino acids replaced, deleted or inserted; in another embodiment, the factor VII variants have no more than 5 amino acids replaced, deleted or inserted; in another embodiment, the factor VIIa variants have no more than 3 amino acids replaced, deleted or inserted compared to wild-type factor VII. In one embodiment, the factor VIIa variants are selected from the list of L305V-FVIIa, L305V/M306D/D309S-FVIIa, L305I-FVIIa, L305T-FVIIa, F374P-FVIIa, V158T/M298Q-FVIIa, V158D/E296V/M298Q-FVIIa, K337A-FVIIa, M298Q-FVIIa, V158D/M298Q-FVIIa, L305V/K337A-FVIIa, V158D/E296V/M298Q/L305V-FVIIa, V158D/E296V/M298Q/K337A-FVIIa, V158D/E296V/M298Q/L305V/K337A-FVIIa, K157A-FVIIa, E296V-FVIIa, E296V/M298Q-FVIIa, V158D/E296V-FVIIa, V158D/M298K-FVIIa, and S336G-FVIIa.

In the present context the three-letter or one-letter indications of the amino acids have been used in their conventional meaning as indicated in table 1. Unless indicated explicitly, the amino acids mentioned herein are L-amino acids. The terminology for factor VIIa variants with amino acid substitutions are as follows. The first letter represent by the one-letter code the amino acid naturally present at a position of human wild-type factor VIIa. The following number represent the position in human wild-type factor VIIa. The second letter represent by the one-letter code the different amino acid substituting for the natural amino acid.

An example is L305V/K337A-FVII, the leucine at position 305 of wild-type factor VIIa is replaced by a valine and the Lysine at position 337 of human wild-type factor VIIa is replaced by an alanine, both mutations in the same Factor VII variant.

TABLE 1

Abbreviations for amino acids:

| Amino acid | Tree-letter code | One-letter code |
|---|---|---|
| Glycine | Gly | G |
| Proline | Pro | P |
| Alanine | Ala | A |
| Valine | Val | V |
| Leucine | Leu | L |
| Isoleucine | Ile | I |
| Methionine | Met | M |
| Cysteine | Cys | C |
| Phenylalanine | Phe | F |
| Tyrosine | Tyr | Y |
| Tryptophan | Trp | W |
| Histidine | His | H |
| Lysine | Lys | K |
| Arginine | Arg | R |
| Glutamine | Gln | Q |
| Asparagine | Asn | N |
| Glutamic Acid | Glu | E |
| Aspartic Acid | Asp | D |
| Serine | Ser | S |
| Threonine | Thr | T |

The term "TF antagonist", as used herein is intended to mean any compound binding directly to TF without reducing or inhibiting apoptosis of a cell population as determined in the apoptosis assay described in example 3 (e.g. FVIIai).

In one embodiment of the invention, the TF antagonist is an antibody against human TF. In one embodiment the antibody is a human antibody. In a further embodiment the antibody is monoclonal antibody. In a further embodiment the antibody is a Fab fragment, F(ab)$_2$ fragment, F(ab')$_2$ fragment, or a single chain Fv fragment In this context, the term "treatment" is meant to include both prevention of an adverse condition and regulation of an already occurring condition with the purpose of inhibiting or minimising the condition. Prophylactic administration of FVIIa or another TF agonist, or FVIIai or another TF antagonist is thus included in the term "treatment". In this context, the term "patient" is defined as any animal, in particular mammals, such as humans. The term "subject" is used interchangeably with "patient".

Conditions, which may be treated, comprises pathological conditions such as, for example, various cancers, various degenerative neurological disorders, neuropathologies including Parkinson's disease, Alzheimer's disease, amyotrophic lateral sclerosis (ALS), denervation atrophy, otosclerosis, stroke, dementia, multiple sclerosis, Huntington's disease and the encephalopathy associated with acquired immunodeficiency disease (AIDS). In tissues such as skin and intestine, which are turned-over continually during the life of an organism, the cells forming these tissues undergo programmed cell death throughout the life of the organism. Normally, this process is tightly regulated and the number of cells produced due to cell division is balanced by the number of cells undergoing programmed cell death. However, the regulation of programmed cell death is a complex process involving numerous pathways and, on occasion, defects occur in the regulation of programmed cell death. Given the critical role of this process in maintaining a steady-state number of cells in a tissue or in maintaining the appropriate cells during development of an organism, defects in programmed cell death often are associated with pathologic conditions.

Various disease states occur due to aberrant regulation of programmed cell death in an organism. For example, defects that result in a decreased level of apoptosis in a tissue as compared to the normal level required to maintain the steady-state of the tissue can result in an increased number of cells in the tissue. Such a mechanism of increasing cell numbers has been identified in various cancers, where the formation of a tumor occurs not because the cancer cells necessarily are dividing more rapidly than their normal counterparts, but because the cells are not dying at their normal rate. In comparison to cancer, where the likelihood of a cell undergoing apoptosis is decreased, various pathologies are associated with tissues containing cells undergoing a higher than normal amount of apoptosis. For example, increased levels of apoptosis are observed in various neuropathologies, including Parkinson's disease, Alzheimer's disease, amyotrophic lateral sclerosis (ALS), denervation atrophy, otosclerosis, stroke, dementia, multiple sclerosis, Huntington's disease and the encephalopathy associated with acquired immunodeficiency disease (AIDS). Since nerve cells generally do not divide in adults and, therefore, new cells are not available to replace the dying cells, the nerve cell death occurring in such diseases results in the progressively deteriorating condition of patients suffering from the disease. Other conditions associated with a higher than normal level of apoptosis, which may be treated with a TF agonist, comprises myopathies and muscular dystrophies, glomerulosclerosis, Monckeberg's medial sclerosis, inflammatory bowel disease, Crohn disease, autoimmune hepatitis, hemochromatosis and Wilson disease, viral hepatitis, alcoholic hepatitis, acute hepatic failure of different etiology, diseases of the bile ducts, atherosclerosis, hypertension and apoptosis associated with the use of chemotherapeutic drugs.

In a first aspect, the invention relates to a method for reducing or inhibiting apoptosis of a cell population, comprising the step of contacting said cells with a tissue factor agonist. In one embodiment the cells are human cells expressing tissue factor, including fibroblasts, smooth muscle cells, tumour cells, haematopoietic cells, monocytes, macrophages, epithelial cells, keratinocytes, nerve cells and endothelial cells.

In a second aspect, the invention relates to a method for inducing or enhancing apoptosis of a cell population, comprising the step of contacting said cells with a tissue factor antagonist. In one embodiment the cells are human cells expressing tissue factor, including fibroblasts, smooth muscle cells, tumour cells, haematopoietic cells, monocytes, macrophages, epithelial cells, keratinocytes, nerve cells and endothelial cells.

In a further aspect, the invention relates to a method of reducing the severity of a condition in an individual characterized by an elevated level of apoptosis by inhibiting or reducing the level of apoptosis of a cell population, the method comprising administering to the individual an effective amount of a pharmaceutical composition comprising Factor VIIa or factor VII or another tissue factor agonist. In one embodiment of the invention the condition characterized by an elevated level of apoptosis is a neurodegenerative disease. In a further embodiment of the invention the disease or condition characterized by an elevated level of apoptosis is selected from the group consisting of Parkinson's disease, Alzheimer's disease. amyotrophic lateral sclerosis (ALS), denervation atrophy, otosclerosis, stroke, dementia, multiple sclerosis, Huntington's disease and the encephalopathy associated with acquired immunodeficiency disease (AIDS), myopathies and muscular dystrophies, glomerulosclerosis, Monckeberg's medial sclerosis, inflammatory bowel disease, Crohn's disease, autoimmune hepatitis, hemochromatosis and Wilson disease, viral hepatitis, alcoholic hepatitis, acute hepatic failure of different etiology, diseases of the bile ducts, atherosclerosis, hypertension, apoptosis induced hair loss and apoptosis associated with the use of chemotherapeutic drugs. In one embodiment the apoptosis associated with the use of chemotherapeutic drugs results in hair loss.

In a further aspect, the invention relates to a method of reducing the severity of a condition in an individual characterized by a reduced level of apoptosis by inducing or enhancing the level of apoptosis of a cell population, the method comprising administering to the individual an effective amount of a pharmaceutical composition comprising a tissue factor antagonist. In one embodiment of the invention the disease or condition characterized by a reduced level of apoptosis is selected from the group consisting of primary tumour growth, tumour invasion, metastasis, psoriasis, an autoimmune disease and restenosis.

In a further aspect, the invention relates to the use of a tissue factor agonist for the manufacture of a medicament for treatment of disease or condition associated with undesired apoptosis of a cell population.

In a further aspect, the invention relates to the use of a tissue factor antagonist for the manufacture of a medicament for treatment of disease or condition, where induction or enhancement of apoptosis of a cell population is desired.

In a further aspect, the invention relates to a method of regulating apoptosis of a cell population, comprising the step of either contacting said cells with a tissue factor agonist or contacting said cells with a tissue factor antagonist.

In one embodiment of the invention the tissue factor agonist is FVII or FVIIa.

In a further embodiment of the invention the tissue factor antagonist is modified FVII. In one embodiment the modified factor VII is selected from factor VII modified with Phe-Phe-Arg chloromethyl ketone, Phe-Phe-Arg chloromethylketone, D-Phe-Phe-Arg chloromethyl ketone, D-Phe-Phe-Arg chloromethylketone Phe-Pro-Arg chloromethylketone, D-Phe-Pro-Arg chloromethylketone, Phe-Pro-Arg chloromethylketone, D-Phe-Pro-Arg chloromethylketone, L-Glu-Gly-Arg chloromethylketone and D-Glu-Gly-Arg chloromethylketone, Dansyl-Phe-Phe-Arg chloromethyl ketone, Dansyl-Phe-Phe-Arg chloromethylketone, Dansyl-D-Phe-Phe-Arg chloromethyl ketone, Dansyl-D-Phe-Phe-Arg chloromethylketone, Dansyl-Phe-Pro-Arg chloromethylketone, Dansyl-D-Phe-Pro-Arg chloromethylketone, Dansyl-Phe-Pro-Arg chloromethylketone, Dansyl-D-Phe-Pro-Arg chloromethylketone, Dansyl-L-Glu-Gly-Arg chloromethylketone and Dansyl-D-Glu-Gly-Arg chloromethylketone.

In another aspect, the present invention relates to a method of detecting drug candidates that regulate apoptosis of a cell population, which method comprise a) culturing a TF expressing cells;
b) measuring the apoptosis of a cell population;
c) incubating the cells with a drug candidate, and
d) measuring the apoptosis of the incubated cells and determining any change in the level of apoptosis compared to the level of apoptosis measured in step b, such change being indicative of biologically active drug candidate in said cell.

The term "TF expressing cell" means any mammalian cell that expresses TF.

The term "drug candidate" is intended to indicate any sample, which has a biological function or exerts a biological effect in a cellular system. The sample may be a sample of a biological material such as a microbial or plant extract, or it may be a sample containing a compound or mixture of compounds prepared by organic synthesis or genetic techniques.

In a further aspect, the invention relates to the use of tissue factor for the protection of cells from apoptosis. As can be seen from the experiments disclosed by the present inventors only cells expressing TF are protected from apoptosis. Thus, in a further aspect, the present invention relates to a method of producing a recombinant protein, the method comprising:

a) transfection of a cell with a polynucleotide constructs encoding TF;
b) transfection of the same cell with a polynucleotide constructs encoding the recombinant protein to be produced;
c) cultivating the cell in an appropriate growth medium under conditions allowing expression of the polynucleotide constructs and recovering the resulting polypeptide from the culture medium.

In one embodiment of the invention, the recombinant protein to be produced is human FVII. In a further embodiment the appropriate growth medium comprises FVIIa.

In a further aspect, the invention relates to a method for reducing or inhibiting apoptosis of a cell population, comprising the step of contacting said cells with an activated coagulation factor.

In a further aspect, the invention relates to a method for reducing or inhibiting apoptosis of a cell population, comprising the step of contacting said cells with thrombin or coagulation factor Xa.

In a further aspect, the invention relates to a method for inducing or enhancing apoptosis of a cell population, comprising the step of contacting said cells with a thrombin inhibitor or a coagulation factor Xa inhibitor.

In a further aspect, the invention relates to a method of reducing the severity of a condition in an individual characterized by an elevated level of apoptosis by inhibiting or reducing the level of apoptosis of a cell population, the method comprising administering to the individual an effective amount of a pharmaceutical composition comprising thrombin or coagulation factor Xa.

In a further aspect, the invention relates to a method of reducing the severity of a condition in an individual characterized by a reduced level of apoptosis by inducing or enhancing the level of apoptosis of a cell population, the method comprising administering to the individual an effective amount of a pharmaceutical composition comprising a thrombin inhibitor or a coagulation factor Xa inhibitor.

In a further aspect, the invention relates to the use of thrombin or coagulation factor Xa for the manufacture of a medicament for treatment of disease or condition associated with undesired apoptosis of a cell population.

In a further aspect, the invention relates to the use of a thrombin inhibitor or a coagulation factor Xa inhibitor for the manufacture of a medicament for treatment of disease or condition, where induction or enhancement of apoptosis of a cell population is desired.

In a further aspect, the invention relates to a method of regulating apoptosis of a cell population, comprising the step of either contacting said cells with thrombin or coagulation factor Xa or contacting said cells with a thrombin inhibitor or a coagulation factor Xa inhibitor.

In one embodiment of the present invention the thrombin inhibitor is hirudin. In another embodiment of the present invention the coagulation factor Xa inhibitor is Tick Anticoagulant Protein (TAP). In a specific embodiment the Tick Anticoagulant Protein is a recombinant human protein.

| Abbreviations: | |
|---|---|
| TF | tissue factor |
| FVII | factor VII in its single-chain, unactivated form |
| FVIIa | factor VII in its activated form |
| rFVIIa | recombinant factor VII in its activated form |
| FVIIai | modified (inactivated) factor VII |
| FFR-FVIIai | factor VII inactivated by reaction with D-Phe-L-Phe-L-Arg chloromethyl ketone |

Tissue factor (TF) is the cellular receptor for factor FVIIa (FVIIa) and the complex is principal initiator of blood coagulation. We have studied the effects of FVIIa binding to TF on cell apoptosis of cells that express high amounts of TF. TF expressing cells incubated with FVIIa is shown to be less sensitive to apoptosis.

Below we show for the first time a clear connection between FVIIa binding to TF and the cell apoptosis. We present data that FVIIa stimulation of TF expressing cells leads to a reduction or inhibition of apoptosis of a cell population. Furthermore, active site-inhibited FVIIa (FFR-FVIIa) is shown to induce or enhance apoptosis of a cell population. TF is constitutively expressed on the plasma membrane of many extravascular cells, such as stromal fibroblasts in vascular adventitia and in fibrous capsules of liver, spleen and kidney. Thus, expression of TF is found at sites physically separated from the circulating blood and providing a haemostatic envelope. Upon injury this barrier is thought to protect the organism against bleeding. TF can, however, be induced in monocytes/macrophages, vascular smooth muscle cells, endothelial cells and in a number of tumour cells by a variety of agents, including cytokines and growth factors. Induction at the transcriptional level occurs rapidly after stimulation, identifying TF as a growth-related immediate early gene.

Not only binding to TF, but also the catalytic activity of TF/FVIIa seem to be mandatory, since active-site inhibited FVIIa did not elicit the protection from apoptosis. We excluded that the protection from apoptosis by FVIIa occurred due to FXa or thrombin, since TAP and Hirudin did not abolish the effect of FVIIa in the apoptosis assay. A dose-response of the anti-apoptotic effect of FVIIa was seen in BHK cells transfected with TF.

The regimen for any patient to be treated with FVIIa or another TF agonist or FVIIai or another TF antagonist as mentioned herein should be determined by those skilled in the art. The daily dose to be administered in therapy can be determined by a physician and will depend on the particular compound employed, on the route of administration and on the weight and the condition of the patient. An effective amount is suitably a daily dosage from about 5 $\mu$g/kg/day to about 500 $\mu$g/kg/day, preferably from about 10 $\mu$g/kg/day to 300 $\mu$g/kg/day, more preferred from about 15 $\mu$g/kg/day to 200 $\mu$g/kg/day, most preferred from about 20 $\mu$g/kg/day to 100 $\mu$g/kg/day.

The FVIIa or another TF agonist or FVIIai or another TF antagonist should be administered in one single dose, but it can also be given in multiple doses preferably with intervals of 4–6–12 hours depending on the dose given and the condition of the patient.

In a particular embodiment the effective amount is a daily dosage from about 5 µg/kg/day to about 500 µg/kg/day of FVIIa or another TF agonist or FVIIai or another TF antagonist.

The FVIIa or another TF agonist or FVIIai or another TF antagonist may be administered intravenously or it may be administered by continuous or pulsatile infusion or it may be administered directly to the relevant site such as, for example, injected directly into a turnout. FVIIa or another TF agonist or FVIIai or another TF antagonist is preferably administered by intravenous injections and in an amount of about 100–100,000 units per kg body weight, and preferably in an amount of about 250–25,000 units per kg body weight corresponding to about 5–500 µg/kg, a dose that may have to be repeated 2–4 times per 24 hours.

Conventional techniques for preparing pharmaceutical compositions, which can be used according to the present invention are, for example, described in Remington's Pharmaceutical Sciences, 1985.

The compositions used according to this invention are prepared by methods known per se by the skilled artisan.

In short, pharmaceutical preparations suitable for use according to the present invention is made by mixing FVII, FVIIa or another TF agonist or FVIIai or another TF antagonist, preferably in purified form, with suitable adjuvants and a suitable carrier or diluent. Suitable physiological acceptable carriers or diluents include sterile water and saline. Suitable adjuvants, in this regard, include calcium, proteins (e.g. albumins), or other inert peptides (e.g. glycylglycine) or amino acids (e.g. glycine, or histidine) to stabilise the purified factor VIIa. Other physiological acceptable adjuvants are non-reducing sugars, polyalcohols (e.g. sorbitol, mannitol or glycerol), polysaccharides such as low molecular weight dextrins, detergents (e.g. polysorbate) and antioxidants (e.g. bisulfite and ascorbate). The adjuvants are generally present in a concentration of from 0.001 to 4% w/v. The pharmaceutical preparation may also contain protease inhibitors, e.g. apronitin, and preserving agents.

The preparations may be sterilised by, for example, filtration through a bacteria-retaining filter, by incorporating sterilising agents into the compositions, by irradiating the compositions, or by heating the compositions. They can also be manufactured in the form of sterile solid compositions, which can be dissolved in sterile water, or some other sterile medium suitable for injection prior to or immediately before use.

The present invention is further illustrated by the following examples that, however, are not to be construed as limiting the scope of protection. The features disclosed in the foregoing description and in the following examples may, both separately and in any combination thereof, be material for realising the invention in diverse forms thereof.

BRIEF DESCRIPTION OF THE DRAWINGS

FIG. 1: Apoptosis illustrated by FITC-dUTP staining of BHK(+TF). Dose-response of FVIIa.

FIG. 2: Apoptosis illustrated by FITC-dUTP staining of BHK wt. Dose-response of FVIIa.

FIG. 3: Apoptosis illustrated by FITC-dUTP staining of BHK(+TF). Involvement of FXa and thrombin inhibitors.

FIG. 4: Apoptosis illustrated by FITC-dUTP staining of BHK wt. Involvement of FXa and thrombin inhibitors.

FIG. 5: Apoptosis illustrated by FITC-dUTP staining of BHK(+TF). Effect of FVIIa and FFR-FVIIa on serum-starvation induced apoptosis.

Identification of apoptotic cells and immunofluorescence staining for TF.BHK(TF) cells deprived of serum for 6 his (A,B), were treated with 20 nM rFVIIa (C,D), 20 nM FFR-FVIIa (E,F) or control medium (G,H). Immunofluorescence staining for TF (green FITC signal) are seen in B, D, F and H. Morphological appearance of apoptotic nuclei were visualized by Hoechst staining of the BHK(TF) cells (A, C, E and G). Note the apoptotic cells (arrows) when BHK(TF) cells were deprived of serum (A,B) or treated with FFR-FVIIa (E,F) compared to the inhibition of apoptosis seen by absences of any apoptotic nuclei when treated with FVIIa (C,D) or control medium (G,H). Bar=50 µm.

FIG. 8: Apoptosis illustrated by FITC-dUTP staining. Dose-dependent anti-apoptotic effect of FVIIa in cells expressing TF. TUNEL analysis by flow cytometry.

FIG. 9: Apoptosis illustrated by FITC-dUTP staining of BHK(+TF) analyzed by TUNEL and flow cytometry. Involvement of FFR-FVIIa. Involvement of FXa and thrombin inhibitors FIG. 10: Time-dependent activation of caspase 3 upon serum deprivation of BHK(+TF) cells. Western blot analysis using anti-caspase 3 ab's. FVIIa show anti-apoptotic effect at all times tested.

FIG. 11: Apoptosis illustrated by activation of caspase 3. Western blot anlysis using anti-caspase 3 ab's. Anti-apoptotic effect of FVIIa only in cells expressing TF.

Figure 12:
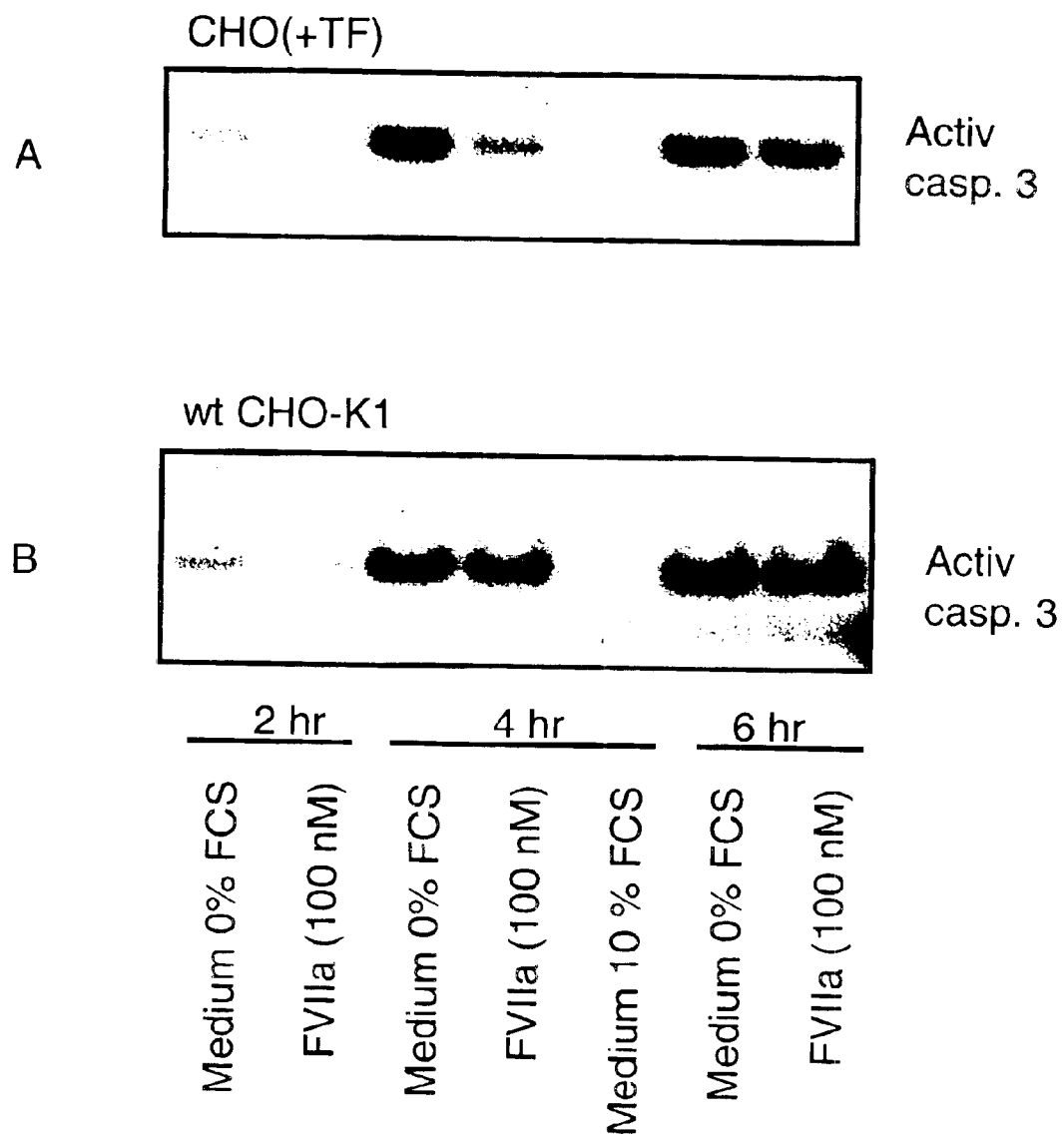

FIG. 12: Apoptosis illustrated by Caspase 3 activation in CHO cells. Western blot analysis using anti-caspase 3 ab's. Effect of FVIIa only in cells expressing TF.

FIG. 13: The anti-apoptotic effect of FVIIa is dose-dependent and correlates with the ability of FVIIa to activate p44/42 MAPK and Akt in BHK(+TF) cells. Western blot analysis.

Figure 14:
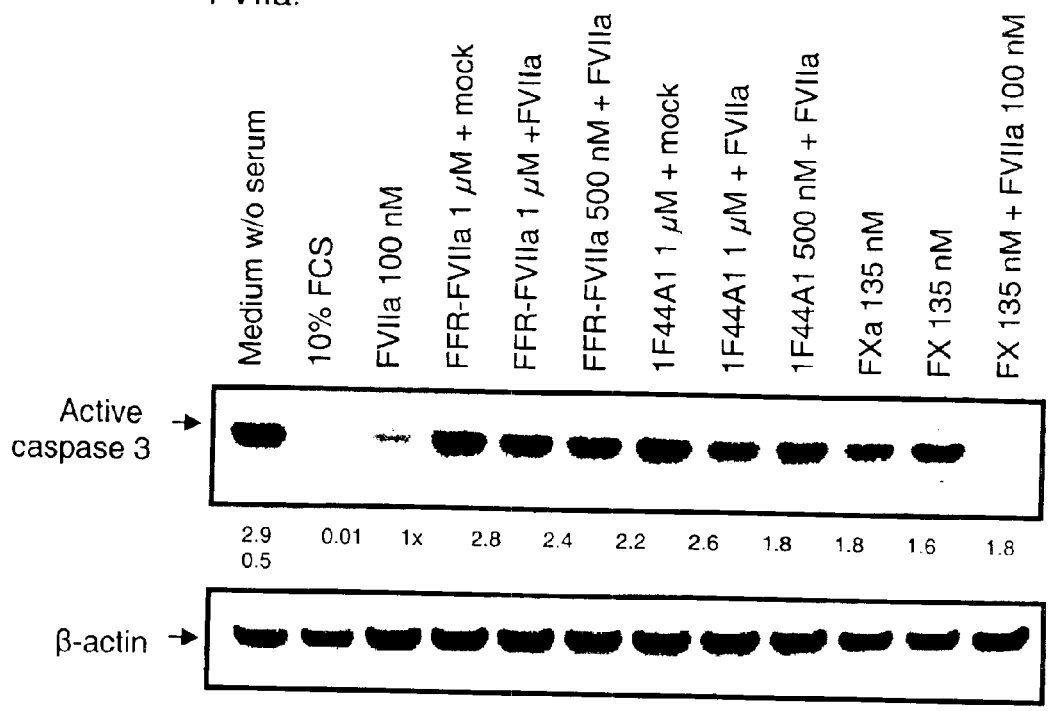

FIG. 14: Apoptosis illustrated by wb analysis of activated caspase 3 in BHK(+TF) cells. Preventing FVIIa from binding to TF neutralizes the anti-apoptotic effect of FVIIa.

EXAMPLES

Example 1

Preparation of FVII

Human purified factor VIIa suitable for use in the present invention is preferably made by DNA recombinant technology, e.g. as described by Hagen et al., Proc.Natl.Acad.Sci. USA 83: 2412–2416, 1986 or as described in European Patent No. 200.421 (ZymoGenetics). Factor VIIa produced by recombinant technology may be authentic factor VIIa or a more or less modified factor VIIa provided that such factor VIIa has substantially the same biological activity for blood coagulation as authentic factor VIIa. Such modified factor VIIa may be produced by modifying the nucleic acid sequence encoding factor VII either by altering the amino acid codons or by removal of some of the amino acid codons in the nucleic acid encoding the natural FVII by known means, e.g. by site-specific mutagenesis.

Factor VII may also be produced by the methods described by Broze and Majerus, J.Biol.Chem. 255 (4): 1242–1247, 1980 and Hedner and Kisiel, J.Clin.Invest. 71: 1836–1841, 1983. These methods yield factor VII without detectable amounts of other blood coagulation factors. An even further purified factor VII preparation may be obtained by including an additional gel filtration as the final purification step. Factor VII is then converted into activated FVIIa by known means, e.g. by several different plasma proteins, such as factor XIIa, IXa or Xa. Alternatively, as described by Bjoern et al. (Research Disclosure, 269 September 1986, pp. 564–565), factor VII may be activated by passing it through an ion-exchange chromatography column, such as Mono Q® (Pharmacia fine Chemicals) or the like.

Example 2

Preparation of FVIIai

Modified factor VII suitable for use in the present invention is made, e.g. as described in International Publications Nos. 92/15686, 94/27631, 96/12800 and 97/47651 ZymoGenetics/Novo Nordisk).

Example 3

To investigate the effect of FVIIa on BHK(+TF) and BHK wt cell survival, apoptosis of cells was induced by serum-starvation for 24 hr and 48 hr. Apoptosis was detected by flow cytometry after Terminal deoxynucleotidyl-transferase dUTP Nick End Labeling (TUNEL). One of the later steps in apoptosis is DNA fragmentation, a process which results from the activation of endonucleases during the apoptotic program. The nucleases degrade the higher order chromatin structure into fragments of approximately 300 kb and subsequently into smaller DNA pieces about 50 bp length. In the TUNEL assay (APO-BRDU from Pharmingen) TdT catalyses a template-independent addition of bromolated deoxyuridine triphosphates (Br-dUTP) to the 3'-hydroxyl termini of double- and single-stranded DNA in paraformaldehyde and ethanol fixed cells. After incorporation these sites are identified by flow cytometric means by staining the cells with a FITC-labeled anti-BrdU mAb. To follow cell-cycle progress, the cells are in the final step labeled labelled-with Propidium Iodine (PI).

Proteins—Human recombinant FVII and FVIIa was expressed and purified as described by Thim, L. et al. Biochem 27: 7785–7793, 1988.

FVIIai was obtained by blocking of FVIIa in the active site with D-Phe-L-Phe-L-Arg chloromethyl ketone (FFR-FVIIa) as previously described by Sorensen B. B. et al. J.Biol.Chem. 272: 11863–11868, 1997.

Thrombin was from Enzyme Research Lab. The specific thrombin inhibitor hirudin may be purchased from Sigma-Aldrich and the specific FXa inhibitor Recombinant TAP (Tick Anticoagulant Protein) was kindly provided by Dr. G. P. Vlasuk, Corvas (San Diego, Calif.). Cell Culture—The baby hamster kidney cell line BHK-21 tk-ts13 (ATCC CRL 1632) was cultured in Dulbecco's modified Eagle's medium containing 10% FCS, 100 IU/ml penicillin, 100 µg/ml streptomycin. All cell lines were grown in T80 or T175 flasks and subcultured into 10 cm single culture dishes (78 cm$^2$).

Transfection of BHK cells with TF—The complete human TF cDNA was cloned into the mammalian Zem219b expression vector. BHK cells were transfected with the TF expression plasmid using the calcium phosphate coprecipitation standard technique. Cells with stably integrated constructs were selected with 1 µM Methotrexate.

Experimental:

The cells were seeded (800,000 cells/dish) in Dulbecco's Modified Eagle's Medium ("DMEM") supplemented with 10% FCS, 100 IU/ml penicillin, 100 µg/ml streptomycin (DMEM+/+). After two days the cells were approximately 80% confluent and ready for serum-starvation. The coils were washed two times with DMEM –/– media (before use DMEM–/– was left in the incubator over night for right pH stabilization and temperature) and after the final wash cells were left with 6 ml DMEM–/– and the indicated compounds for 24 hr and/or 48 hr. At the end of the incubation period the loose cells in the media was pooled with the trypsin-treated adhered cells and centrifuged at 300×g for 5 min. Cells were washed with PBS before fixation in 1% paraformaldehyde in PBS on ice for 15 mm. Hereafter cells were washed in PBS and resuspended in 500 µl PBS before addition of 5 ml 70% EtOH. The cell-suspension was left for at least 18 hr at –20° C. before being analyzed by TUNEL assay accordingly to the manufactures procedures (APO-BRDU™ from Pharmingen).

Results:

Dose-response of the anti-apoptotic effect of FVIIa in BHK(+TF) and BHK wt cells. In BHK(+TF) cells apoptosis was induced by serum-starvation for 24 hr or 48 hr and apoptotic cells were detected by TUNEL staining and flow cytometry. The results are presented as FITC-labelled DNA-breaks (FITC-dUTP) on a log x-scale (the more right shift in the x-axis value the more DNA-breaks in the cell) and the y-axis depicts cell number on a linearly scale. BHK(+TF) cells were serum-starved in the presence of increasing concentrations of FVIIa (from 12.5 nM to 100 nM). When BHK(+TF) cells was left for 24 hr in serum-deprived media a clear increase in the number of apoptotic cells (FIG. 1A) was seen as a decrease in the peak representing healthy cells (10% serum) grown in the presence of 10% serum. The remaining four curves in FIG. 1A represent increasing concentration of FVIIa, and the results show that as low concentration as 12.5 nM FVIIa was able to rescue the cell population from apoptosis. In FIG. 1B BHK(+TF) cells were keep in serum-deprived media for 48 hr with increasing concentration of FVIIa. In this experiment there was a very clear increase in apoptotic cells seen by comparing non-treated with 10% serum treated cells. After 48 hr the non-treated cells were more apoptotic than after 24 hr serum-deprivation. A very clear dose-dependent inhibition of apoptosis was seen with FVIIa after 48 hr serum-starvation. At 100 nM FVIIa almost total suppression of apoptosis was seen.

Effect of TAP and Hirudin on FVIIa Induced Inhibition of Apoptosis

Since a significant effect of FVIIa was seen in this assays, it was important to determine if this apoptosis-suppressive effect is specific to FVIIa or if down-stream coagulation products could account for these findings. Therefore BHK (+TF) cells were serum-starved for 24 hr or 48 hr in the presence of FVIIa (100 nM) with or without the specific thrombin inhibitor hirudin (25 U/ml) and the specific FXa inhibitor TAP(100 nM). As a control thrombin (10 nM) with or without hirudin+TAP was also tested. FIG. 3A show that non-treated cells at 24 hr serum-deprivation resulted apoptotic cells by a decreased in FITC-dUTP "healthy peak" and a slight right-shift of the peak compared to healthy serum-treated cells represented by the black line. Here FVIIa showed totally inhibition of apoptosis and this effect is not influenced by addition of hirudin and TAP, indicating that FXa and FIIa are not involved in the FVIIa induced protection from apoptosis. As a control experiment cells were serum-starved in the presence of 10 nM FIIa. FIIa was to the same extend as FVIIa able to inhibit apoptosis. By adding FIIa and hirudin+TAP simultaneously this inhibition of apoptosis is abolished and the cells show clearly increase in apoptotic cells by right-shift in FITC-dUTP, resulting in an extra peak. At 48 hr of serum-starvation the non-treated (FIG. 3B) cells are more apoptotic compared to 24 hr serum-starvation. In this experiment FVIIa independently of hirudin and TAP partly inhibited apoptosis. The same degree of apoptosis-inhibition was seen with FIIa. A concentration of 10 nM FVIIa (FIG. 3B) was not enough to inhibit apoptosis during 48 hr serum-starvation. In conclusion both at 24 hr and 48 hr of serum-starvation FVIIa's anti-apoptotic effect is independent of the down-stream coagulation products FXa and FIIa.

BHK wt cells were also investigated in the same experiment exploring the effect of specific inhibitors o(downstream coagulation products on the anti-apoptotic effect of FVIIa. When BHK wt cells were serum-starved for 24 hr there was no increase in apoptotic cells (FIG. 4A) compared to 10%-treated cells and this correlates well with the experiment shown in FIG. 2A. Serum-starvation for 48 hr of BHK wt cells (FIG. 4B) clearly resulted in an increase in apoptotic cells compared to healthy cells (FIG. 4B). In this experiment FVIIa at 100 nM with or without hirudin and TAP and FVIIa at 10 nM had no anti-apoptotic effect (FIG. 4B). It was very clear that FIIa showed the same anti-apoptotic effect on BHK wt coils (FIG. 4B) as on BHK(+TF) cells (FIG. 3B).

Proteolytic Activity of FVIIa is Mandatory for the Anti-apoptotic Effect.

In order to investigate if binding of FVIIa to TF was enough to induce this anti-apoptotic effect an active site-inactivated variant of FVIIa (FFR-FVIIa) was added to the cells during the starvation period. FFR-FVIIa binds with a two fold higher affinity to TF but leaves the complex proteolytically inactive. FIG. 5 depicts an experiment employing BHK(+TF) cells where FVIIa at both 24 hr (FIG. 5A) and 48 hr (FIG. 5B) serum-starvation had a clear apoptosis-suppressive effect. Interestingly FFR-FVIIa (FIG. 5C) was not able to rescue any cells and the population of cells was identical to non-treated cells both at 24 hr and 48 hr of serum-deprivation.

Time-dependency of Serum-starvation Induced Apoptosis in BHK(+TF) Cells.

Figure 6:
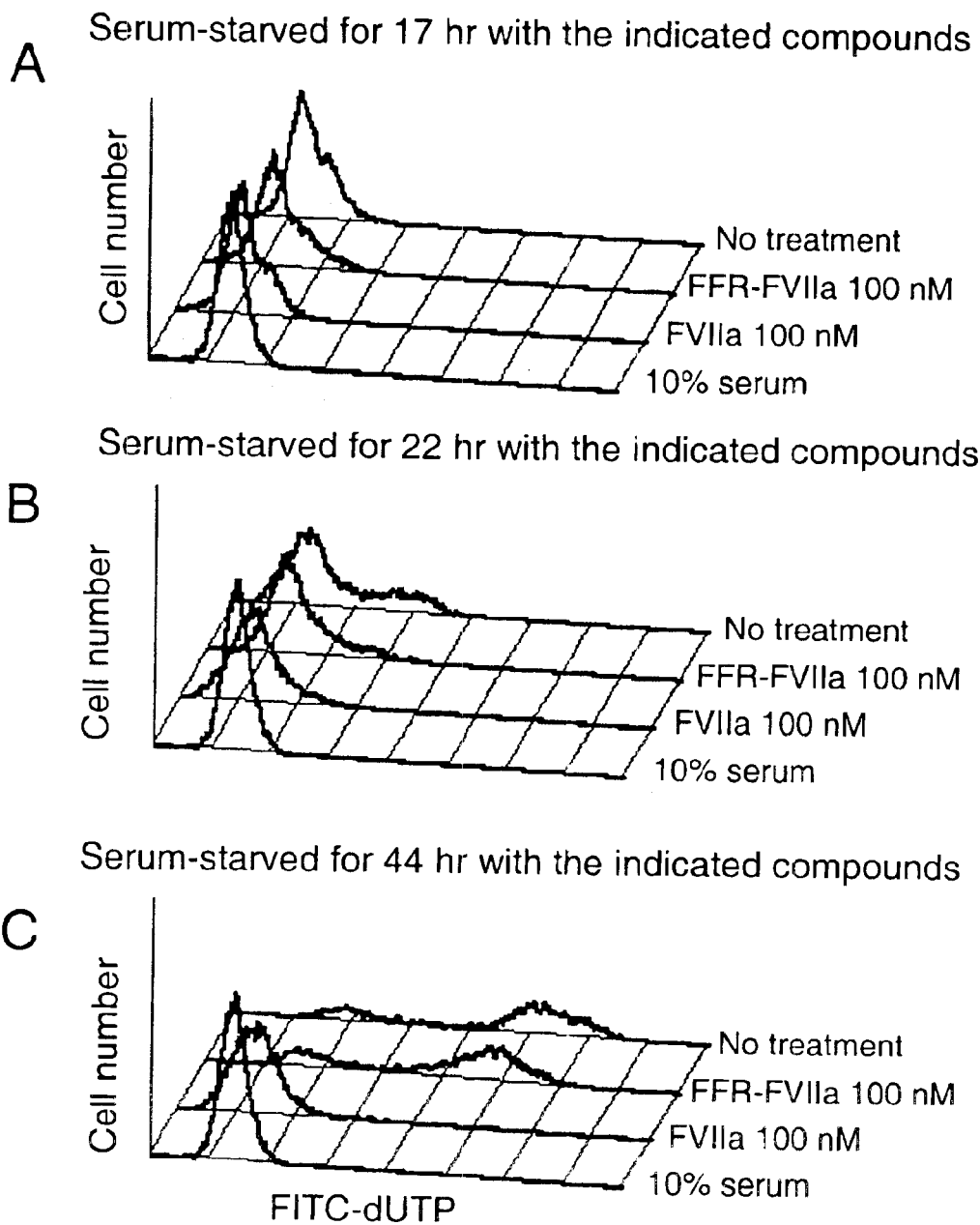
FIG. 6: Apoptosis illustrated by FITC-dUTP staining of BHK(+TF). Time-dependency of serum-starvation induced apoptosis.

TUNEL staining of apoptotic cells will only detect late-stage apoptosis since DNA-breaks must be formed. BHK(+TF) cells were serum-starved for 17, 22, and 44 hr with or without FVIIa and FFR-FVIIa. In the experiment 10% serum was employed as control of healthy cells and no-treatment as an apoptosis-positive control. From FIG. 6 it is seen that 22 hr (panel B) of serum-starvation was minimum time to induce measurable apoptosis by labelling DNA-breaks with the TUNEL assay. When the cells were grown for 17 hr (panel A) in serum-deprived media no significant amount of apoptosis was seen. In contrast 44 hr of serum-starvation very clearly induced apoptosis in this assay. From FIG. 6 it is also clear that FVIIa but not FFR-FVIIa show anti-apoptotic effects after 44 hr of serum-deprivation.

Example 4

Recombinant human FVIIa and FFR-FVIIa were prepared as described in example 1 and 2. Factors X, FXa, thrombin and hirudin were obtained from Enzyme Research Laboratories (South Bend, Ind). The specific FXa inhibitor, recombinant tick anticoagulant protein (TAP), was a generous gift from Dr. Vlasuk (Corvas, La Jolla, Calif.). Antibodies against caspase 3, phosphorylated p44/42 MAPK, and phosphorylated Akt were from Cell Signaling Technology (Boston, Mass.). β-actin antibody was from Abcam (Cambridge, UK). LY294002 and U0126 were from Promega (Madison, Wis).

Cell lines—The Baby Hamster Kidney cell line BHK-21 tk⁻ (ATCC CRL 1632) was cultured in DMEM containing 10% FCS, 100 IU/ml penicillin, and 100 µg/ml streptomycin. The complete human TF cDNA was cloned into the mammalian Zem219b expression vector and transfected into BHK cells using the calcium phosphate coprecipitation procedure and stably integrated constructs were selected using 1 µM methotrexate (Sorensen) B. B., Freskgard, P.-O. Nielsen, L. S., Rao, L. V. M., Ezban, M., and Petersen, L. C. (1999) J.Biol.Chem. 274, 21349–21354). Chinese hamster ovary (CHO-K1, ATCC CCL-61) cells were cultured in Ram-F12 medium supplemented with 10% FCS and 1% non-essential amino acids. CHO cells were transfected with the complete human TF in the pcDNA3 (Invitrogen, Carlsbad, Calif.) using a sterile-filtered blend of non-liposomal transfection-promoting lipids in 80% ethanol (FUGENE™ (Roche Diagnostics, Indianapolis, Ind.). Stable cell lines were selected by resistance to geneticin (0.7 mg/ml). Clonal cell lines were tested for TF expression in a FXa generation assay employing intact monolayers of cells. The expression of functional TF in the two transfected cell lines BHK(+TF) and CHO(+TF) were comparable as judged by the FXa generation assay.

TUNEL/flow cytometry—The cells were seeded in 9 cm dishes (800,000 cells/dish) in DMEM supplemented with 10% FCS, 100 IU/ml penicillin, and 100 µg/ml streptomycin. When cells were approximately 80% confluent, they were subjected to serum deprivation in the presence and absence of experimental compounds. Briefly, the monolayers were washed twice with DMEM (before use the DMEM was left in the incubator over night for pH stabilization) and after the final wash the cells were overlaid with 6 ml DMEM containing the experimental test compounds for 24 or 48 h. At the end of the incubation period, the loose cells in the media were collected and pooled with the trypsin-detached adhered cells, and centrifuged at 300×g for 5 min. The cells were washed with PBS before fixation in 1% paraformaldehyde in PBS on ice for 15 min. After the fixation, the cells were washed in PBS and resuspended in 500 µl PBS before adding 5 ml of 70% EtOH. The cell suspension was left for at least 18 h at −20° C. before they were analyzed by TUNEL assay (APO-BRDU™, BD Biosciences Pharmingen, San Diego, Calif.) following the procedure described in the manufacturer's technical bulletin. Stained cells were analyzed by a FACSCAN™ flow cytometer (Becton Dickinson).

Detection of caspase 3 activation—Cells were cultured in 9-cm dishes and serum deprived in the presence or absence of experimental test compound as described under TUNEL. At the end of specific time interval, as indicated in Results, the cultured dish was placed on ice and the overlaying medium containing loose cells was collected. The adhered cells were scraped from the bottom of the dish and pooled with the conditioned medium and centrifuged at 300×g for 5 min at 4° C. to obtain the cell pellet. The supernatant was discarded and the tubes were drained carefully (by inverting the tubes) to obtain the cell pellet. The cells were lysed by adding 50 µl of ice-cold Chaps Cell Extract Buffer (50 mM Pipes/KOH, pH 6.5, 2 mM EDTA, 0.1% Chaps, supplemented immediately prior to use with 20 µg/ml Leupeptin, 10 µg/ml aprotinin, 5 mM DTT, 0.1 mM AEBSF (4-(2-Aminoethyl)-bezenesulfonylfluoride)). The lysates were frozen and thawed three times, centrifuged at 15,000×g for 5 min at 4° C. The supernatant was collected and total protein concentration was determined by Bio-Rad protein assay kit. Approximately 10 µg of protein was subjected to SDS-PAGE on 4–12% gradient gel under reducing conditions. Caspase 3 activation was evaluated by western blot analysis using an antibody against caspase 3 that recognizes both the zymogen (33 kDa) as well as the cleaved antigen (18 kDa).

Determination of Akt and p44/42 MAP kinase activation—Cells were seeded in the complete medium in 6-well plates. When the cells reached 80–90% confluency, the cells were washed twice in serum free medium and left in serum free medium for 2 h to make the cells quiescent. Cells were stimulated with FVIIa for 10 min at 37° C. Where inhibitors were included, they were added to the cells 30 min prior to the addition of FVIIa. After the 10 min treatment with FVIIa, the cells were lysed in Lysis buffer (20 mM Tris, 0.1% (v/w) Triton X-100, 1 mM EDTA, 1 mM EGTA, 50 mM sodium-fluoride, 10 mM sodium β-glycerophosphate, 5 mM sodium pyrophosphate, 0.1 mM AEBSF (4-(2-Aminoethyl)-bezenesulfonylfluoride), 1 mM benzamidine, 150 mM NaCl, pH 7.5. Added just before use: 1 mM sodium orthovanadate, 5 µg/ml leupeptin, 10 µg/ml aprotinin). Ten µg protein was loaded on to SDS-PAGE (4–12% gradient gel, reducing condition) and subjected to western blot analysis using specific antibodies against phosphorylated p44/42 MAPK and cAkt.

Western blot analysis—After electroblotting, the membranes were blocked in blocking buffer (TBS containing 0.1% Tween-20 and 5% non-fat dry milk) for 1 h and washed 3 times in TBS with 0.1% Tween-20 (TBS/T) before adding the primary antibody (1:1000, and for β-actin 1:1,000,000) in the blocking buffer. After overnight incubation with the primary antibody at 4° C., the membranes were washed 3 times in TBS/T before adding the HRP-conjugated secondary antibody (1:2000) in the blocking buffer. Membranes were incubated for 1 hr at room temperature before washing thrice with TBS/T. Chemiluminescence substrate (Supersignal, Pierce) was added for 5 min and the chemiluminescence was detected by a cooled CCD-camera (LAS1000, Fujifilm). These digital images were used to quantify the intensity of the bands using Image Gauge v. 4.0 (Fujifilm).

Immunocytochemistry—BHK(+TF) cells were seeded in 8-chamber glass slides (Nalge Nunc International, Rochester, N.Y.) and grown to 30% confluence. Cells were washed and incubated with serum free medium supplemented with none, 20 nM FVIIa, 20 nM FFR-FVIIa, or 10% FCS for 6 hr. At the end of the experiment cells were washed, fixed in 4% (v/v) paraformaldehyde in phosphate-buffered saline (PBS) for 15 min. at 4° C., briefly rinsed in PBS, post-fixed in 70% (v/v) ethanol for 15 min at RT, and air-dried. Antigen retrieval was achieved by microwave oven (Polar Patent, Umeå, Sweden) pre-treatment in 10 mM citrate buffer pH 6.0 preheated to 60° C. for 3×5 min at 80% effect. The cells were cooled for 10 min in the citrate buffer at room temperature, rinsed in Tris-buffered saline (TBS), pre-incubated for 15 minutes in 5% donkey serum in TBS, followed by incubation with goat anti-human TF IgG (American Diagnostica Incorporation, Greenwich, Conn.) overnight at 4° C. The cells were then incubated with biotinylated donkey anti-goat (Jackson ImmunoReseach Laboratory, West Growe, PE) for 1 hr, HRP-streptavidin (NEN Life Science Products, Boston, Mass.) for 30 min, and TSA-FITC (Tyramide Signal Amplification Fluorescein system) (NEN Life Science Products, Boston, Mass.). Following a brief rinse in TBS the cells were counterstained with Hoechst (Molecular Probes, Leiden, The Netherlands) for morphological analyses of apoptotic cells, rinsed in H₂O and mounted with Mounting Medium Fluorescence (DAKO, Glostrup, Denmark). The cells were photographed using an Olympus BX51 reflected fluorescence system microscope equipped with selective AMCA and FITCH filters, and, a DP50 digital camera.

Figure 7:
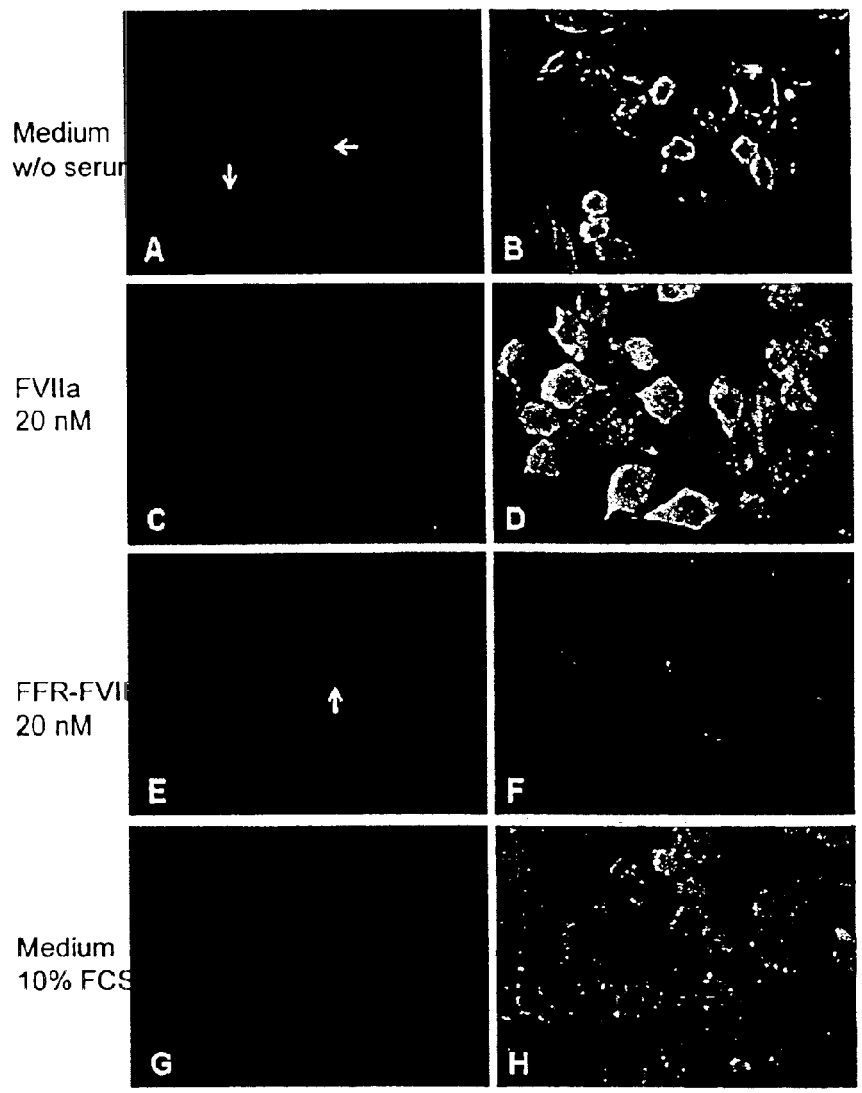
FIG. 7: Apoptosis illustrated by Hoechst staining of condensed nuclei (marked with an arrow) in BHK(+TF) cells.

Results:

FVIIa prevents nuclei chromatin condensation under serum-free conditions. The inventors of the present invention have found out, that upon serum-deprivation, BHK(+TF) cells tend to round up, loosely adhere to culture dishes (detach easily from the dish) and undergo subtle morphological changes. These changes were diminished, when FVIIa was included in serum-free medium. The present invention is based on the examined effect of FVIIa and FFR-FVIIa on cell viability and apoptosis, where cells were examined for apoptotic morphology changes. Under serum-starvation conditions (FIG. 7, panels A and B), fluorescence microscopy revealed that a considerable number of BHK(+TF) cells were characterized by apoptotic blebs and nuclei with chromatin-condensed bodies, whereas the presence of FVIIa during serum starvation markedly decreased the number of cells with apoptotic morphology (FIG. 7, panels C and D) such that cell cultures exposed to FVIIa had an appearance similar to those maintained in serum containing medium (FIG. 7, panels G and H). In contrast to FVIIa, FFR-FVIIa failed to prevent nuclei condensation induced by serum deprivation (FIG. 7, panels E and F) suggesting that the proteolytic activity of FVIIa was essential for this effect.

Anti-apoptotic effect of FVIIa under serum-deprived conditions—The cell morphology observations in FIG. 7 suggested that exposure of FVIIa to serum starved BHK(+TF) cells produces an anti-apoptotic effect. To obtain a quantitative characterization of this effect we examined the cells for apoptotic changes measuring DNA degradation by means of TUNEL/flow cytometry. Compared to the serum control, culturing of BHK(+TF) cells in serum-free conditions for 24 hr markedly increased the fraction of apoptotic cells with advanced DNA degradation (FIG. 8A) and this fraction was slightly increased with prolonged serum starvation to 48 hr (FIG. 8B). Notably, however, the cells were rescued from apoptosis in a dose dependent manner upon addition of 1 pM to 100 nM FVIIa to the serum-deprived medium. The anti-apoptotic effect of FVIIa was evident at 1 nM with substantially increased cell survival at 10 nM FVIIa; that is at a concentration equivalent to the FVII plasma level. An increase to 100 nM FVIIa slightly improved cell survival further. A similar profile of anti-apoptotic effect of FVIIa was observed in cells exposed to FVIIa for 48 h (FIG. 8B).

Wild-type, non-transfected BHK cells, do not express detectable levels of TF. Like TF-transfected cells, culture of these cells under serum free conditions for 48 hr resulted in extensive apoptosis as demonstrated by the TUNEL assay. However, FIG. 8C shows that in contrast to BHK(+TF) cells, wild-type BHK cells could not be rescued from apoptosis by FVIIa suggesting that binding to TF is essential for its anti-apoptotic effect.

The observation that FVIIa but not active site blocked FVIIa, FFR-FVIIa, was able to preserve BHK(+TF) cells from the morphological changes induced by serum starvation prompted us to explore this further with the TUNEL assay. Next, It was establish that FVIIa proteolytic activity is required for its anti-apoptotic effect. The results shown in FIG. 9A clearly indicated that the activity is essential since FVIIa, but not FFR-FVIIa, protected BHK(+TF) cells from apoptosis.

Like FVIIa, the down-stream proteases of the TF coagulation pathway, FXa and thrombin, are known to induce intracellular signaling producing various cellular responses. It was therefore important to rule out that FVIIa exerted its effect through generation of small amounts of down-stream coagulation factors. Although we have used recombinant FVIIa in these studies and found no evidence for the generation of FXa or thrombin in our experimental system, we evaluated the anti-apoptotic effect of FVIIa in the presence of specific inhibitors of both FXa and thrombin, i.e., TAP and hirudin, respectively. As shown in FIG. 9B, TAP and hirudin failed to prevent the anti-apoptotic effect of FVIIa whereas they completely abolished the anti-apoptotic effect of FXa and thrombin. These data establishes that the specific protease activity of FVIIa/TF is responsible for the reduction in apoptosis observed in TF expressing cells exposed to FVIIa.

Figure 10:
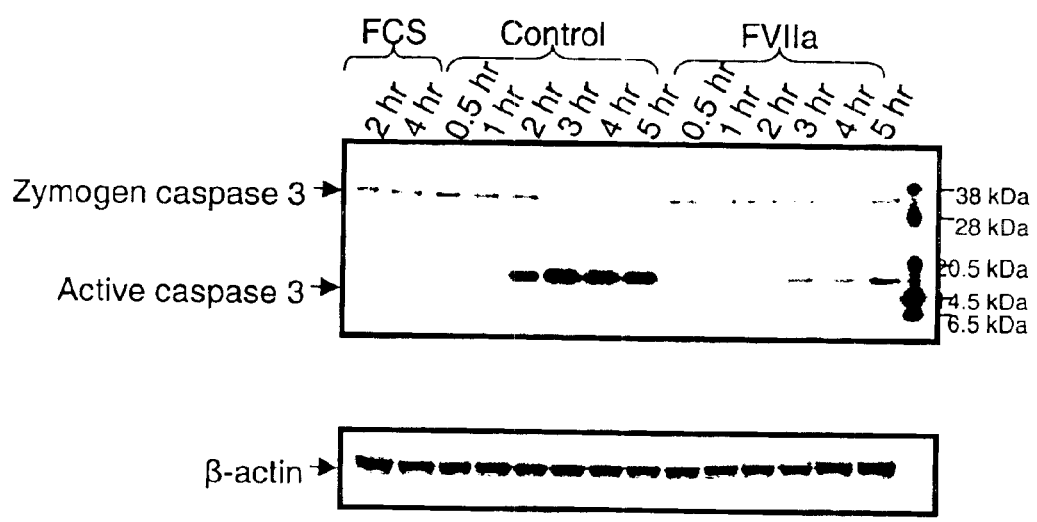

FVIIa suppresses caspase 3 activation—Caspases, a family of cysteine proteases, are central regulators of apoptosis. Caspases are synthesized as latent zymogens organized in cascade systems that upon activation stimulate apoptosis. Inhibition of apoptosis is accomplished either by inhibiting the activity of caspases or by preventing their activation. To obtain clues on the mechanism by which FVIIa inhibits apoptosis, we investigated the activation of the central apoptosis effector, caspase 3, by Western blot analysis using an antibody that recognizes the zymogen as well as the activated enzyme form. Serum removal induced a time-dependent appearance of a 18–20 kDa caspase 3 band in BHK(+TF) cells (FIG. 10). Caspase 3 activation was evident 2 hr after serum deprivation and reached a maximum at 3 hr. The activation was maintained for at least 5 hr (the duration of the experiment). However, the presence of 100 nM FVIIa in the serum free medium clearly attenuated caspase 3 activation with 70–80% at 3, 4, and 5 hr. In additional experiments (data not shown), FVIIa induced a dose-dependent inhibition of caspase 3 activation, which correlated with the dose-dependent inhibition of apoptosis measured in TUNEL assay. In contrast to BHK(+TF) cells, FVIIa failed to inhibit caspase 3 activation in wild type BHK cells that do not express TF (FIG. 11B). Serum abolished the activation of caspase 3 in both BHK(+TF) and wild-type BHK cells. Similar data were obtained with wild type CHO-K1 and TF-transfected CHO cells (FIG. 12).

FVIIa/TF was shown in quiescent BHK(+TF) cells to activate p44/42 MAPK (FIG. 13A) as well as Akt (FIG. 13B), and both are considered important players in survival signaling. However it is currently not clear which kinase is responsible for the anti-apoptotic effect of FVIIa. Experiments with the specific MEK inhibitor U0126 and the specific PI3-kinase inhibitor LY294003 indicates that both kinases might be involved in the anti-apoptotic effect of FVIIa (data not shown).

To verify that the anti-apoptotic effect of FVIIa was mediated through TF, antagonists of FVIIa-TF interaction (FFR-FVIIa and mAb 1F44A1) were preincubated with the cells before addition of FVIIa in serum-free medium. Apoptosis was detected by caspases-3 activation. FFR-FVIIa and the monoclonal anti-human TF antibody 1F44A1 were able to attenuate the anti-apoptotic effect of FVIIa (FIG. 14).

What is claimed is:

1. A method of treating an autoimmune disease characterized by a reduced level of apoptosis comprising administering to an individual in need of such treatment an amount of a composition comprising a tissue factor antagonist and a pharmaceutically acceptable carrier effective to treat the autoimmune disease.

2. The method of claim 1, wherein the autoimmune disease is psoriasis.

3. The method of claim 1, wherein the tissue factor antagonist is modified factor VII.

4. The method of claim 3, wherein the modified factor VII is selected from the group consisting of factor VII modified with: Phe-Phe-Arg chloromethylketone, D-Phe-Phe-Arg chloromethylketone, Phe-Pro-Arg chloromethylketone, D-Phe-Pro-Arg chloromethylketone, L-Glu-Gly-Arg chloromethylketone, D-Glu-Gly-Arg chloromethylketone, Dansyl-Phe-Phe-Arg chloromethylketone, Dansyl-D-Phe-Phe-Arg chloromethylketone, Dansyl-Phe-Pro-Arg chloromethylketone, Dansyl-D-Phe-Pro-Arg chloromethylketone, Dansyl-L-Glu-Gly-Arg chloromethylketone, and Dansyl-D-Glu-Gly-Arg chloromethylketone.

5. The method of claim 1, wherein the tissue factor antagonist is an antibody against human tissue factor.

6. A method for regulating apoptosis in a cell population comprising contacting the cell population with a recombinant, purified recombinant, or purified tissue factor agonist and a recombinant, purified recombinant, or purified tissue factor antagonist.

7. The method of claim 5, wherein the tissue factor agonist is FVII or FVIIa.

8. The method of claim 5, wherein the tissue factor antagonist is modified FVII.

9. The method of claim 5, wherein the tissue factor antagonist is an antibody against human tissue factor.

10. The method of claim 8, wherein the modified factor VII is selected from the group consisting of factor VII modified with: Phe-Phe-Arg chloromethylketone, D-Phe-Phe-Arg chloromethylketone, Phe-Pro-Arg chloromethylketone, D-Phe-Pro-Arg chloromethylketone, L-Glu-Gly-Arg chloromethylketone, D-Glu-Gly-Arg chloromethylketone, Dansyl-Phe-Phe-Arg chloromethylketone, Dansyl-D-Phe-Phe-Arg chloromethylketone, Dansyl-Phe-Pro-Arg chloromethylketone, Dansyl-D-Phe-Pro-Arg chloromethylketone, Dansyl-L-Glu-Gly-Arg chloromethylketone, Dansyl-D-Glu-Gly-Arg chloromethylketone.

* * * * *